(12) United States Patent
Kobylecki

(10) Patent No.: US 8,357,340 B2
(45) Date of Patent: Jan. 22, 2013

(54) MATERIALS ANALYSIS

(75) Inventor: Ryszard Jurek Kobylecki, Ely (GB)

(73) Assignee: Wicken Technology Limited, Cambridgeshire (GB)

(*) Notice: Subject to any disclaimer, the term of this patent is extended or adjusted under 35 U.S.C. 154(b) by 1219 days.

(21) Appl. No.: 10/569,321

(22) PCT Filed: Aug. 16, 2004

(86) PCT No.: PCT/GB2004/003538
§ 371 (c)(1),
(2), (4) Date: Jan. 8, 2007

(87) PCT Pub. No.: WO2005/019814
PCT Pub. Date: Mar. 3, 2005

(65) Prior Publication Data
US 2007/0149022 A1    Jun. 28, 2007

(30) Foreign Application Priority Data
Aug. 19, 2003  (GB) .................................. 0319457.8

(51) Int. Cl.
*B01D 35/00* (2006.01)
*B01L 99/00* (2010.01)

(52) U.S. Cl. ........ 422/535; 422/501; 422/513; 422/527; 422/534

(58) Field of Classification Search .................. 422/513, 422/534, 501, 527, 535
See application file for complete search history.

(56) References Cited

U.S. PATENT DOCUMENTS

| | | | |
|---|---|---|---|
| 3,620,675 A | 11/1971 | Olson | |
| 4,594,902 A * | 6/1986 | Compton et al. | 73/863.23 |
| 5,127,278 A | 7/1992 | Benz | |
| 5,142,920 A | 9/1992 | Bart et al. | |
| 5,552,325 A * | 9/1996 | Nochumson et al. | 436/177 |
| 5,841,975 A * | 11/1998 | Layne et al. | 709/203 |
| 5,908,995 A | 6/1999 | Pauchon et al. | |
| 6,004,822 A | 12/1999 | Li et al. | |
| 6,375,028 B1 * | 4/2002 | Smith | 220/258.1 |
| 2002/0014106 A1 * | 2/2002 | Srinivasan et al. | 73/23.42 |
| 2003/0088369 A1 * | 5/2003 | Hughes | 702/25 |

FOREIGN PATENT DOCUMENTS

| | | |
|---|---|---|
| EP | 1 308 710 A2 | 5/2003 |
| EP | 1308724 | 5/2003 |
| FR | 2.057.343 | 4/1971 |
| JP | 020038941 | 2/1990 |
| SU | 1101297 A | 7/1984 |

* cited by examiner

*Primary Examiner* — In Suk Bullock
*Assistant Examiner* — Paul Hyun
(74) *Attorney, Agent, or Firm* — Fay Sharpe LLP

(57) ABSTRACT

A materials analysis device (2) comprises an inner receptacle (4), incorporating a filter (5) at its lower end, within an outer receptacle (6). Gas inlet/outlet ports (8, 10) are arranged to provide a means whereby solvent can be caused to pass between the receptacles (4, 6) via filter (5). Solvent in the receptacles (4, 6) is arranged to be heated and its temperature assessed. In use in one embodiment, a solute material to be analyzed is introduced into outer receptacle (6) and a solvent is introduced into inner receptacle (4). The solvent is caused to pass back and (15) forth between the receptacles (4, 6) via the filter (5) until a saturated solution of the solute is present in inner receptacle (4). This may be removed for analysis. By undertaking the process described at a range of temperatures, a solubility profile for the solute can be determined.

19 Claims, 4 Drawing Sheets

MATERIALS ANALYSIS

This application is a national phase application of and claims priority from international application PCT/GB04/03538 filed on Aug. 08, 2004, fully incorporated herein by reference.

This invention relates to materials analysis and particularly, although not exclusively, relates to a device for analysing materials and a method relating to the same.

The determination of accurate solubility and its relevance to polymorphic composition is becoming of ever-greater importance to the materials science industry and especially to the pharmaceuticals industry. It is recognised that polymorphic modification can change bulk properties such as solubility, bioavailability, colour of pigments and so forth. Furthermore, novel polymorphs of drug substances with unexpected properties can be very commercially important. Devices are available to measure dissolution rates of substances such as drug materials to mimic in vivo dissolution in the stomach or intestines. These generally mimic the parts of the body in terms of their size and obtaining data on new substances on a similar scale would require large amounts of materials and would prove difficult, time consuming and prohibitively expensive.

It is an object of the present invention to address problems associated with materials analysis.

According to a first aspect of the present invention, there is provided a device for analysing a material, comprising:
a first receptacle;
a second receptacle, said first and second receptacles being arranged for the passage of fluid therebetween;
a filtration means arranged to filter fluid passing between said first and second receptacles;
heating means for heating fluid in the device; and temperature assessment means for assessing the temperature of fluid in the device.

Said first receptacle is preferably elongate; the ratio of its average internal diameter to its internal length is preferably less than 0.5, more preferably less than 0.3, especially less than 0.1. Said ratio may be at least 0.01. Said first receptacle preferably has a substantially constant cross-section along its extent. Said first receptacle preferably has a substantially circular cross-section. Said first receptacle is preferably substantially cylindrical.

Said first receptacle preferably includes a first gas port whereby gas can be injected into and/or withdrawn therefrom. When said receptacle is elongate, said first gas port preferably extends transverse to the elongate axis of said receptacle. Said first gas port is preferably provided towards a first end of the receptacle. Preferably, the ratio of the distance of the first gas port from said first end to the distance of it from a second end of the receptacle (wherein said second end is at an opposite end of the receptacle and said first and second ends are suitably spaced apart in the direction of the elongate axis of the receptacle) is less than 0.5, preferably less than 0.2. Said ratio is preferably at least 0.01.

Said device preferably includes a first fluid inlet arranged to allow fluid to be input and/or withdrawn from the first receptacle whilst the first receptacle is in its operative position as part of the device. Preferably, said first fluid inlet includes sealing means whereby it may be sealed after input/withdrawal of fluid and substantially prevent escape of gas which, in use, may be introduced into the device to cause fluid to pass between the first and second receptacles.

Said first receptacle preferably incorporates said filtration means. Said filtration means may be releasably secured to the first receptacle. Preferably, said filtration means is not releasably secured to the first receptacle; preferably, it is substantially a permanent part of the first receptacle. In one embodiment, said filtration means may comprise a metal filter element fixed to other parts of the first receptacle. In another embodiment, it may comprise a sintered material which is fixed to the first receptacle. When the receptacle includes first and second ends as described, preferably said filtration means is at or adjacent to the second end. Said filtration means preferably defines a part of an outer wall of the first receptacle. Preferably, said filtration means defines the second end of the receptacle. Preferably, said first receptacle has an outlet at said second end and, suitably, the filtration means substantially fills the outlet. Preferably, said filtration means is positioned. wholly within the confines of the cross-section of the first receptacle. Thus, the maximum diameter of the filtration means, measured in a direction transverse to the direction of fluid flow therethrough in use, is preferably the same as or less than the diameter of the first receptacle in the region thereof in which the filtration means is disposed.

When the device includes first and second ends as described, said first and second ends preferably define respective upper and lower ends of the device. Said filtration means preferably defines a lower wall of the first receptacle.

A gap is preferably defined between the filtration means and said second receptacle. Said filtration means is preferably positioned within the second receptacle but preferably does not abut the second receptacle to any extent.

Said first receptacle is preferably arranged within the second receptacle. Said second receptacle preferably defines an internal volume between its internal walls and said first receptacle preferably defines an external volume, wherein suitable at least 10%, preferably at least 25%, more preferably at least 40%, especially at least 60% of the external volume of the first receptacle is contained within the internal volume of said second receptacle. Said second receptacle preferably includes first and second spaced apart ends. The distance between the second end of the second receptacle and said filtration means is preferably less than the distance between the first end of the second receptacle and said filtration means. When the first receptacle includes first and second ends the first ends of the first and second receptacles are suitably closer to one another than the first end of one is to the second end of the other. Said first and second ends of the second receptacle are preferably spaced from the filtration means. Respective walls which define said first and second ends are preferably spaced from said filtration means.

Said second receptacle preferably includes a second gas port which is preferably closer to the first end of the second receptacle than it is to the second end of the second receptacle. When the first receptacle includes an elongate axis, said second gas port preferably extends tranverse to said axis. Preferably, said second receptacle is elongate and preferably its axis of elongation extends substantially parallel to the axis of elongation of said first receptacle.

A first sealing means is preferably provided between said first receptacle and an adjacent part of the device. Said first sealing means preferably extends around the first receptacle and preferably defines an endless sealing means such as an O-ring. Said first sealing means is preferably resiliently mounted on the first receptacle. When said first and second receptacles include respective first and second gas ports, said first sealing means is preferably arranged between the first and second gas ports to prevent the passage of gas, in use, directly from one port to the other port. Said first sealing means is preferably provided at a position on said first receptacle which is between said first gas port and said filtration means.

When said device includes first and second gas ports, a gas travel path is preferably defined from said first gas port via said first receptacle and via said second receptacle to said second gas port. Said first and second gas ports are preferably arranged so that the flow of gas can be controlled therein to control the flow of fluid between said first and second receptacles via said filtration means.

Said second receptacle preferably includes first securement means for securing it, suitably releasably securing it, to a first housing part of the device. When the device includes first and second gas ports, said first housing part preferably includes openings which communicate with said first and second ports. A second sealing means is preferably arranged between said second receptacle and said first housing part. Said first housing part may include a fluid inlet/outlet port which is aligned with a fluid inlet of the first receptacle. Said first housing part may be releasably securable to a second housing part which suitably surrounds said first housing part and may include openings for communication with said first and second gas ports. Said first and second receptacles (preferably said second housing part) is/are preferably releasably securable to a housing part (hereinafter "said third housing part") which preferably houses one or preferably both of said heating means and said temperature assessment means.

Said heating means is preferably arranged to heat fluid in the first and/or second receptacles. Said heating means preferably comprises a heatable body which is in direct thermal contact with said second receptacle. Said heatable body is preferably thermally coupled to a heat source, for example an electrical heating element. Said heatable body may be made out of metal. Said second receptacle preferably fits within the heatable body, suitably with a wall of the second receptacle, suitably an elongate wall thereof, in contact with a wall of the heated body.

Said heating means is preferably thermostatically controlled.

Said device may include cooling means for reducing the temperature of fluid in said first and/or second receptacles at a rate which is greater than the rate of cooling which would take place under ambient conditions. Said cooling means may comprise means for causing an airflow over the first and/or second receptacles, and may comprise a fan. Said cooling means may alternatively or additionally comprise a heat sink or a source of cold.

Said temperature assessment means is preferably arranged to assess the temperature of fluid in the first and/or second receptacles. It is preferably closer to the second receptacle than the first receptacle. When the device includes a heatable body said temperature assessment means may be arranged to assess the temperature of the heatable body in a region thereof which is adjacent to the first and/or second receptacles. It will be appreciated that, at equilibrium, the temperature of the heated body and that of fluid in the first and second receptacles should be substantially identical.

Said temperature assessment means is preferably a thermometer, for example a platinum resistance thermometer.

Said device preferably includes control means arranged to control operation of said heating means in dependence upon the temperature assessed by said temperature assessment means.

Said device preferably includes means for causing fluid to move back and forth between said first and second receptacles across said filtration means.

According to a second aspect of the invention, there is provided an assembly comprising a device according to the first aspect, wherein said first and/or said second receptacles contain a material to be analysed and a fluid, especially a liquid, in which preferably said material is at least partially soluble.

Said device preferably includes first and second gas ports as described according to said first aspect, wherein preferably said first and second ports are coupled to a gas supply and arranged in one configuration to cause liquid to flow from said first receptacle via said filtration means to said second receptacle; and, in a second configuration, to flow from said second receptacle via said filtration means to said first receptacle. Said device is preferably arranged for oscillation of liquid between the first and second receptacles, suitably at a frequency of at least 5, preferably at least 10 to 20, more preferably at least 30-60 back and forth movements per minute.

Said assembly preferably includes a control device, for example a computer, for controlling operation of the heating means in dependence upon the temperature assessed by said temperature assessment means. Said assembly may include means, for example said computer, for storing data relating to temperature and time during operation of the device. A said computer preferably controls oscillation of liquid between the first and second receptacles. The assembly may include a robot for delivering liquid, for example a solvent, to the device and/or for withdrawing liquid, for example a solution, from the device.

The assembly may include sample receptacles for receiving samples removed from the device, wherein said sample receptacles may include a dilution liquid.

According to a third aspect of the present invention, there is provided an assembly comprising a plurality of devices according to the first aspect (for example 5 to 20 devices) controlled by a computer and preferably arranged as described according to the second aspect.

According to a fourth aspect of the present invention, there is provided a method of analysing a material, the method comprising:

causing a fluid which includes said material to pass back and forth between first and second receptacles via a filtration means;

heating fluid in the first and/or second receptacles;

assessing the temperature of fluid in the first and/or second receptacles;

withdrawing a sample from the first and/or second receptacles.

The method of the fourth aspect may use the device and/or assembly of the first, second and/or third aspects.

In a first embodiment, the method is for assessing the solubility of the material in a solvent. Preferably, the method is for constructing a solubility versus temperature profile of the material. The method preferably comprises heating fluid to a first temperature whilst in contact with the material and taking a first sample of fluid suitably after equilibration. The first sample is suitably a saturated solution of the material in the solvent at the first temperature. The first sample may be analysed to assess the amount of material dissolved in it. The first sample may be diluted to obviate crystallisation prior to analysis.

Preferably, in the method, said first material is initially introduced into one of either said first or second receptacles. Said first sample (and preferably each subsequent sample) is suitably taken from the other receptacle. In a preferred embodiment, the material under analysis is initially introduced into the second receptacle and a sample (which will suitably be a saturated solution) is subsequently taken from the first receptacle. Preferably the material is introduced so that it is in excess over the total amount of solvent present in the first and second receptacles so that the excess is in equilibrium with its saturated solution.

In constructing a solubility versus temperature profile, the method preferably comprises operating the heating means to cause the fluid in the first and/or second receptacles to be heated to a second temperature after said first sample has been taken. Preferably, the device is equilibrated at the second temperature and a second sample taken. Preferably, the temperature is raised at least one, preferably at least three, more preferably at least five, especially at least ten, further times and successive second to eleventh samples are taken and analysed.

Preferably, before the taking of any new sample and whilst heating is taking place fluid is caused to pass back and forth between the first and second receptacles as described to facilitate equilibration of material and fluid. Preferably, during substantially the entirety of the time when the heating means is operative, fluid is caused to cycle back and forth as described.

In the method, fluid is caused to move back and forth as described by causing alternate positive and negative pressure across the filtration means.

In a second embodiment, the method may be for investigating the existence of polymorphs of the material. In such a method, a known concentration of material in a solvent may be subjected to a predetermined heating/cooling regime. After completion of the regime, the solid material which may be crystalline may be analysed. The second embodiment may follow the construction of a solubility versus temperature profile in accordance with the first embodiment. Armed with this profile, material and solvent may be introduced into the device, the temperature fixed and the device allowed to equilibrate. The method then comprises causing the saturated solution to pass through the filter into the first or second receptacle as appropriate (i.e. the solution is separated from the undissolved material). Since the temperature will be known, it will be possible to calculate the concentration of the material in the saturated solution. Thus, by varying the temperature within the device, the method can be used to quickly and easily prepare a wide range of different concentrations of material in the solvent in one of the receptacles. The solution prepared is held in the receptacle in which it has been prepared and can then be subjected to a predetermined temperature profile to encourage formation of a particular polymorph. The method can then be repeated, with a view to preparing different polymorphs using a different concentration of material in the solvent (prepared by selecting an appropriate temperature for preparation of the initial saturated solution) and/or by subjecting the material to a different predetermined temperature profile and/or controlling the polarity of the solution by adding a further solvent of lower polarity designed to lower the solubility and/or undertaking the investigation using a saturated solution of the material in an alternative solvent.

Advantageously, the method of the second embodiment allows analysis of material subjected to the predetermined temperature profile without transferring the material from the receptacle in which it is prepared. For example, the receptacle in which it is prepared may be arranged to be directly introduced into an analysis device (e.g. a XRD device) and the method may, therefore include the steps of removing the first or second receptacle from device and introducing the appropriate receptacle into an analytical device.

The invention extends to a method of constructing a solubility versus temperature profile for a material using the device and/or method described.

The invention extends to a method of investigating polymorphs of a material using the device and/or method described.

Any feature of any aspect of any invention or embodiment described herein may be combined with any feature of any aspect of any other invention or embodiment described herein mutatis mutandis.

Specific embodiments of the invention will now be described, by way of example, with reference to the accompanying diagrammatic drawings, in which.

Figure 1:
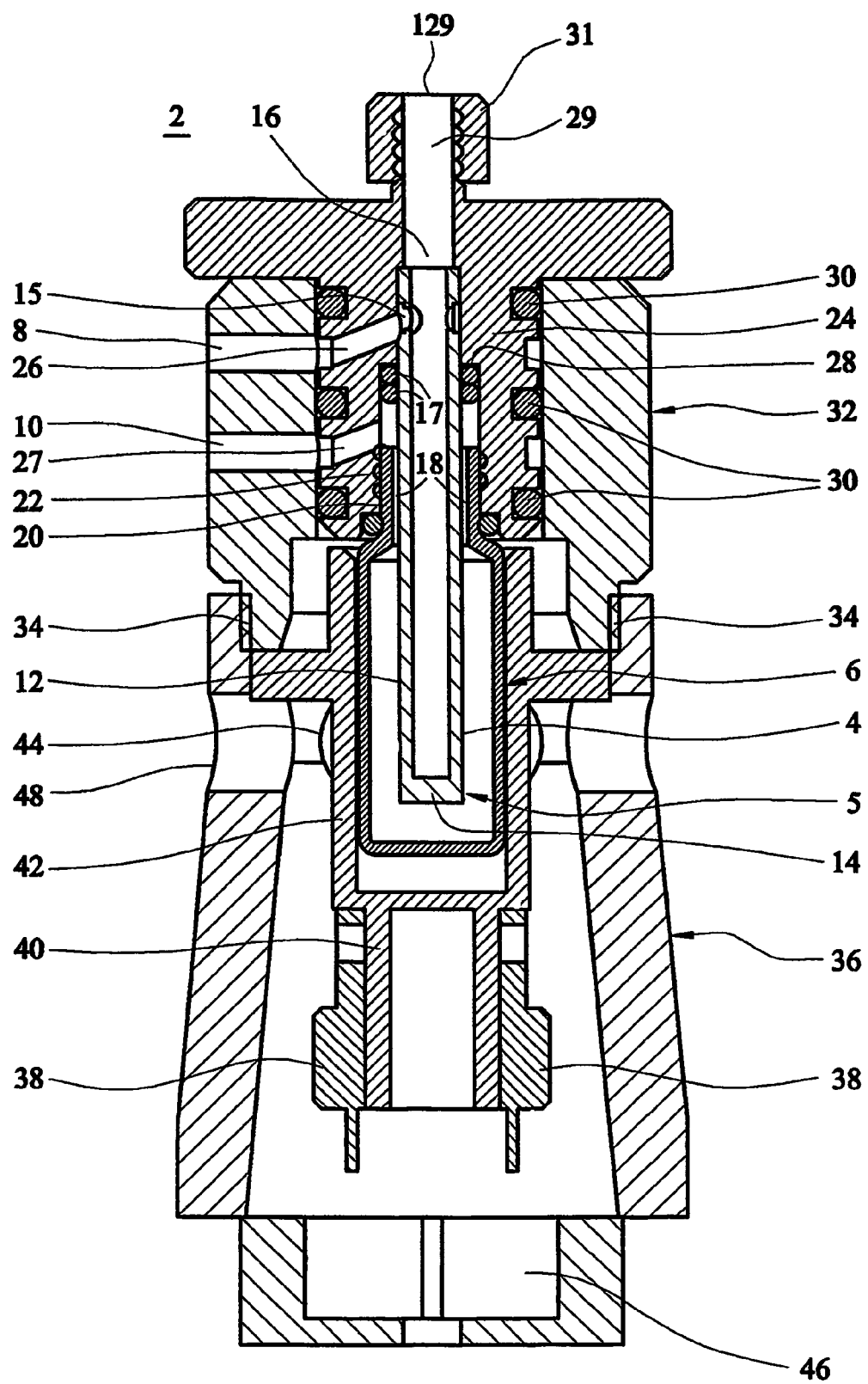
FIG. 1 is a cross-section through a materials analysis device.

Referring to FIG. 1, the materials analysis device 2 comprises an inner receptacle 4, incorporating a filter 5 at its lower end, within an outer receptacle 6. Gas inlet/outlet ports 8, 10 are arranged to provide a means whereby solvent can be caused to pass between the receptacles 4, 6 via filter 5. Solvent in the receptacles 4, 6 is arranged to be heated and its temperature assessed. In use in one embodiment, a solute material to be analysed is introduced into outer receptacle 6 and a solvent is introduced into inner receptacle 4. The solvent is caused to pass back and forth between the receptacles 4, 6 via the filter 5 until a saturated solution of the solute is present in inner receptacle 4. This may be removed for analysis. By undertaking the process described at a range of temperatures, a solubility profile for the solute can be determined.

Features of the device and its uses are described in detail below.

The inner receptacle 4 comprises a thin walled stainless steel cylindrical tube 12 of approximate length 45-50 mm and with a 5 mm outside diameter. At its lower end, the tube is closed by frit 14 of sintered stainless steel of appropriate porosity and dimensions so that it defines filter 5. Typically, the filter may have an average pore size in the range 5 to 20 μm. Towards its upper end, the tube includes O-rings 17 and an opening 15 which is arranged to allow gas to be injected into the tube 12 via port 8. At its upper end 16, the tube is open.

Figure 2:
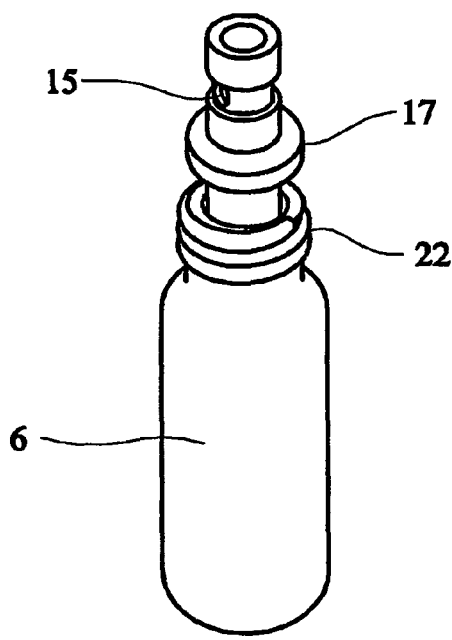
FIG. 2 is a perspective view through a receptacle assembly.
Figure 5:
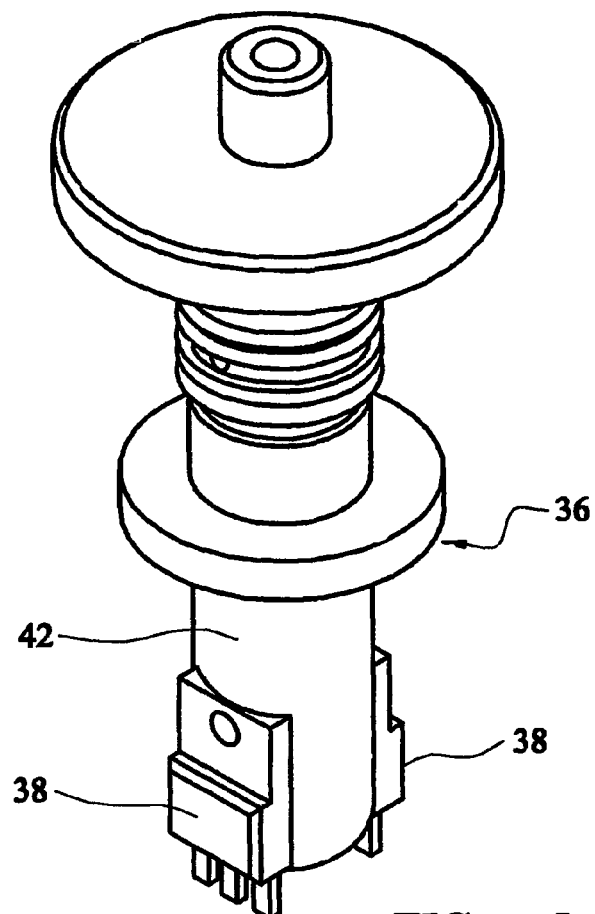
FIG. 5 is a perspective view of the assembly of FIG. 4 secured to a lower body.
Figure 3:
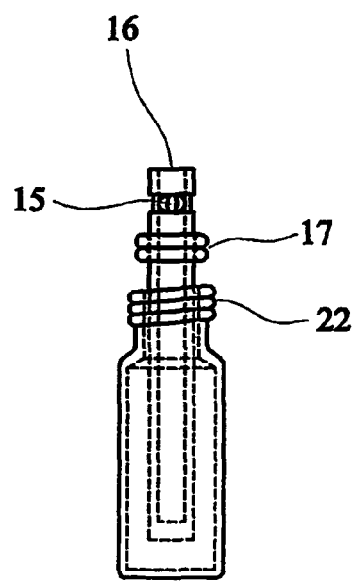
FIG. 3 is a cross-section through the receptacle assembly of FIG. 2.

The tube 12 is arranged within outer receptacle 6, as shown in FIGS. 2 and 3, so that an annular gap 18, via which gas may flow, is defined between it and a neck 20 of receptacle 6. The receptacle 6 may conveniently be a standard chromatographic vial having a threaded portion 22.

Figure 4:
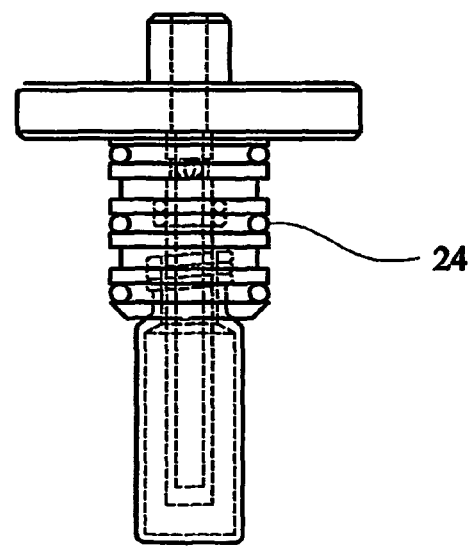
FIG. 4 is a cross-section through an assembly comprising the assembly of FIGS. 2 and 3 secured to an upper module inner body.
Figure 6:
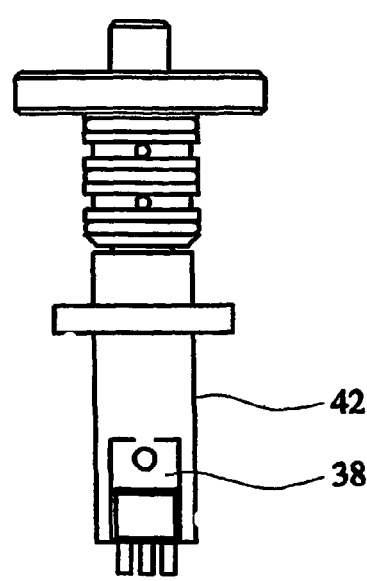
FIG. 6 is a side view of the assembly of FIG. 5.
Figure 9:
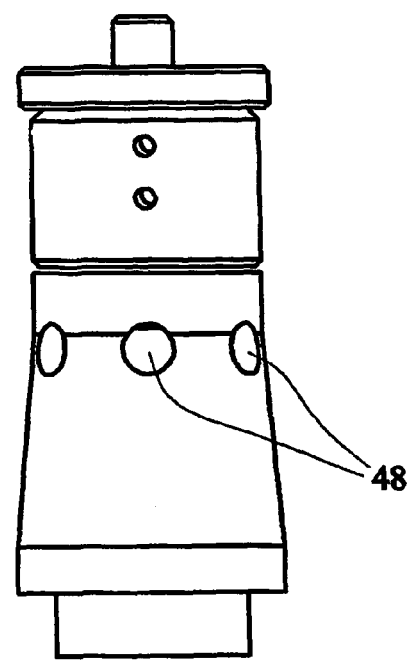
FIGS. 8 and 9 are respectively a perspective view and a side elevation of the complete device.
Figure 7:
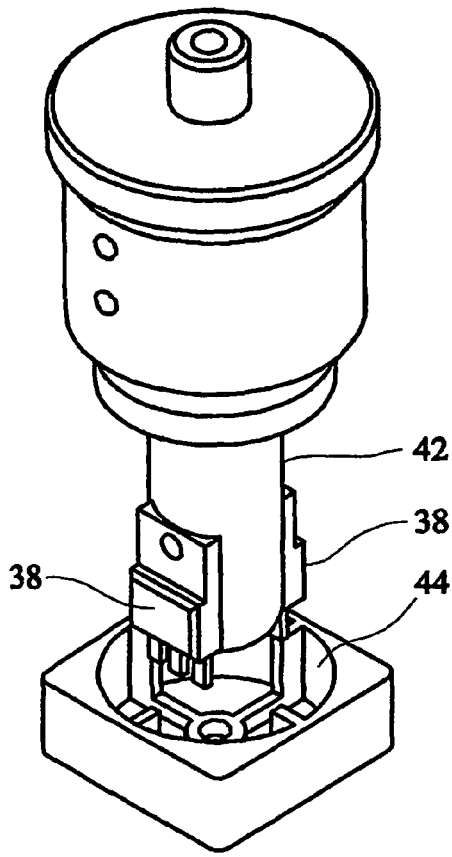
FIG. 7 is a perspective view of the assembly of FIG. 6 incorporating an outer sleeve and showing part of a cooling fan of the assembly.
Figure 8:
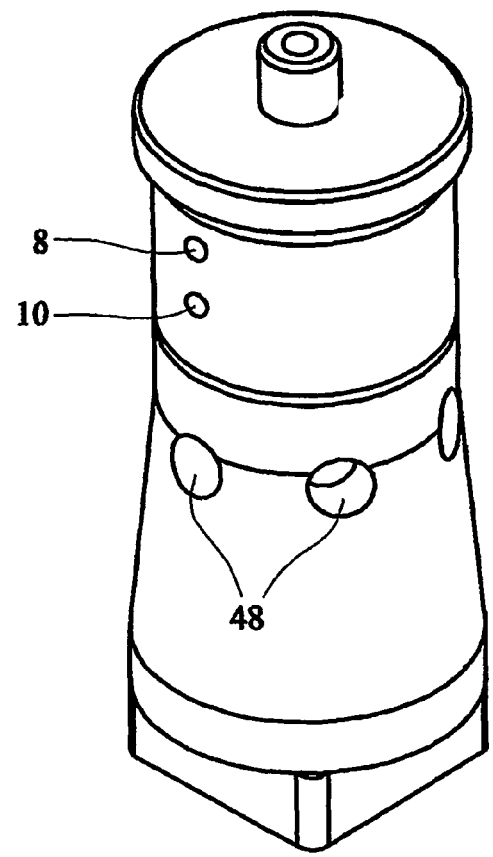

The assembly of FIGS. 2 and 3 is screw-threadedly is connected, via threaded portion 22, to an upper module body 24 as shown in FIGS. 1 and 4. The body 24 includes a first asymmetric cross-channel 26 which is aligned with opening 15 in the receptacle 4 and with port 8 so that gas can pass through port 8 and via channel 26 and opening 15 into the receptacle 4. The body 24 includes a second asymmetric cross-channel 27 which is aligned with port 10 and is in fluid communication with gap 18 defined between inner and outer receptacles 4, 5. The body 24 also defines a seat 28 which sealingly engages O-rings 17 and prevents gas from passing directly between ports 8 and 10 without passing into the receptacle 4.

At its upper end, body 24 includes an access-port 29 for delivery of solvent into receptacle 4. This port is closed at its upper end by a screw cap 31 which includes a self-sealing piercable needle seal 129.

An outer sleeve 32 is a press fit on the body. The sleeve 32 includes ports 8 and 10 which are isolated from one another by O-rings 30 mounted on the body 24.

At its lower end in region 34, sleeve 32 is externally screw-threaded and is arranged to be releasably secured to a lower body 36 which incorporates heating elements 38 which are thermally coupled to receptacle 6 via metal housing parts 40, 42 so that solvent in receptacle 6 can be heated. A platinum resistance thermometer 44 is arranged to assess temperature adjacent receptacle 6 for determining the temperature of solvent at equilibrium therein.

The lower body 36 includes a fan (represented generally by reference numeral 46) at its lower end which is arranged to facilitate cooling of solvent in the apparatus. The lower body 36 also incorporates ventilation holes 48. Additionally, the lower body may incorporate a heat sink or a source of cold to further facilitate cooling of the solvent.

Ports 8, 10 are arranged to be connected to a driving gas supply. Input of gas via the respective ports into the device 2 is controlled by a pair of remote electronically driven solenoid operated valves (or equivalent)(not shown). Alternate closing and opening of the valves on a cyclic basis is used to drive solvent back and forth across the filter 5. Thus, when the valve which controls flow of gas to port 8 is opened to the driving gas supply and the valve which controls flow of gas to port 10 is vented, any solvent in receptacle 4 will be driven across filter 5 into receptacle 6. Then, before the fluid is driven from receptacle 6 and out of the device via port 10, the valve which controls the flow of gas to port 8 is open to venting and that which controls the flow to port 10 is opened to the driving gas supply so solvent is driven from receptacle 6 via filter 5 and back into receptacle 4. Thus, by opening and closing valves sequentially as described and at an appropriate frequency (e.g. in the range 30-60 back and forth movements per minute), solvent can pass through filter 5 in a tidal-type fashion on a constant cycle basis.

The device 2 may be used to measure solubility of a test solute in a selected solvent as follows. Firstly, a clean dry receptacle 6 (which may conveniently be a standard chromatographic vial as described above) is selected and an unweighed portion of the test solute is placed in it. Clearly, the identity of solute and solvent combination under analysis will define approximately how much solute should be used, but within this limitation it does not need to be weighed.

Next, the device is assembled as shown in FIG. 1 with receptacle 4 within the receptacle 6 which contains the test solute.

Temperatures at which solubility measurements are to be taken (referred to as "temperature set points") are determined manually or by a computer using boiling point information related to the solvent being used. In either case, data relating to them is stored in a computer which controls operation of the device, a robot and so on.

A robotically controlled needle picks up a predetermined volume of the selected solvent from a given solvent tray, travels to the centre of port 29 and inserts and injects the solvent into receptacle 4 via the piercable needle seal 129. The solenoid valves are caused to operate to cause the tidal-type back and forth flow of solvent, and consequently, the solvent will pass through filter 5 into receptacle 6 thereby to contact the test solute.

Then, a heating cycle, controlled by the computer, is commenced wherein heating elements 38 are operated according to a preset cycle and heat is conducted therefrom to heat the solvent in receptacle 6. The temperature is initially set say 10° C. higher than ambient. The resistance thermometer 44 then measures the temperature, compares it to a first temperature set point and then the heating elements 38 or cooling fan 46 (or other cooling device(s)) are operated as appropriate to heat/cool the solvent to the first temperature set point. When the device reaches a steady state acceptable temperature (as determined by thermometer 44), the driving gas supply and solenoid valves are operated to cause the solvent (and any solute dissolved therein) to pass back and forth across the filter 5. This has the effect of mixing solvent and solute so that a saturated solution of the solute in the solvent is formed. After equilibration, the valves controlling supply of gas via ports 8, 10 are operated so that the saturated solution passes into receptacle 4. It will be appreciated that undissolved solute will be held back from entering receptacle 4 by the filter 5. A fixed, small known volume of solution is abstracted from receptacle 4 by robotically controlled aspiration using a needle inserted into receptacle 4 via port 29. The sample is delivered to one of a series of sample vials loaded with a known amount of a diluting solvent (in which the sample is highly soluble) for immediate or subsequent analysis. The use of a diluting solvent obviates crystallisation of the sample which might occur if the sample is not diluted. Analysis can be used to determine solubility of the solute in the solvent at the first temperature set point.

Figure 10:
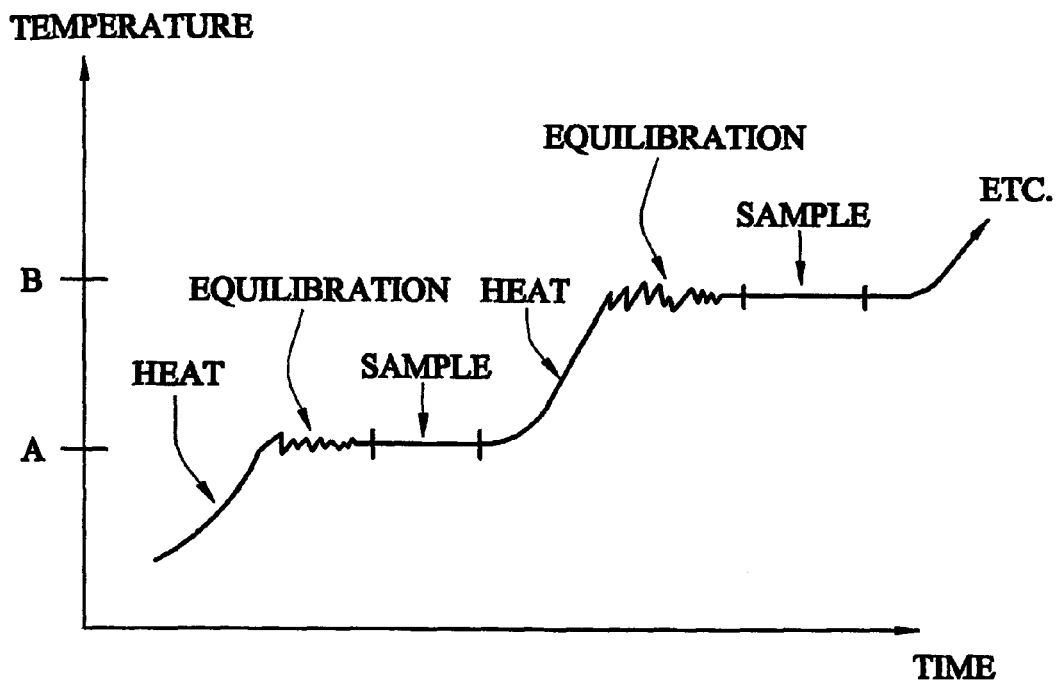
FIG. 10 is a graph of temperature vs time to illustrate a typical heating cycle to which a solvent/solute may be subjected in the device.

The abovedescribed sequence of steps is repeated for second (and subsequent) temperature set points on the remaining solvent/solute in the device. Part of a typical heating cycle to which solvent/solute in the device may be subjected is schematically illustrated in FIG. 10. Each cycle comprises heating and equilibration steps prior to sampling when solvent/solute are at equilibrium at respective first, second (and subsequent) temperature set points A, B etc.

Analysis of samples withdrawn from the device may be undertaken using any suitable method, such as evaporative light scattering (els), uv, ir, nmr spectroscopy, hplc, glc, by flame ionisation or by any other appropriate analytical technique. The use of els is preferred.

Analysis is suitably undertaken to determine the amount of solute in the sample vials. Since the amount of diluting solvent is known, the amount of solute in a sample removed from the device can be calculated. This may be scaled against a solution of the solute of a standard concentration in a solvent in which it is readily soluble (e.g. MeoH, $CH_2Cl_2$/$MeoH_2$ or MeCN).

Figure 11:
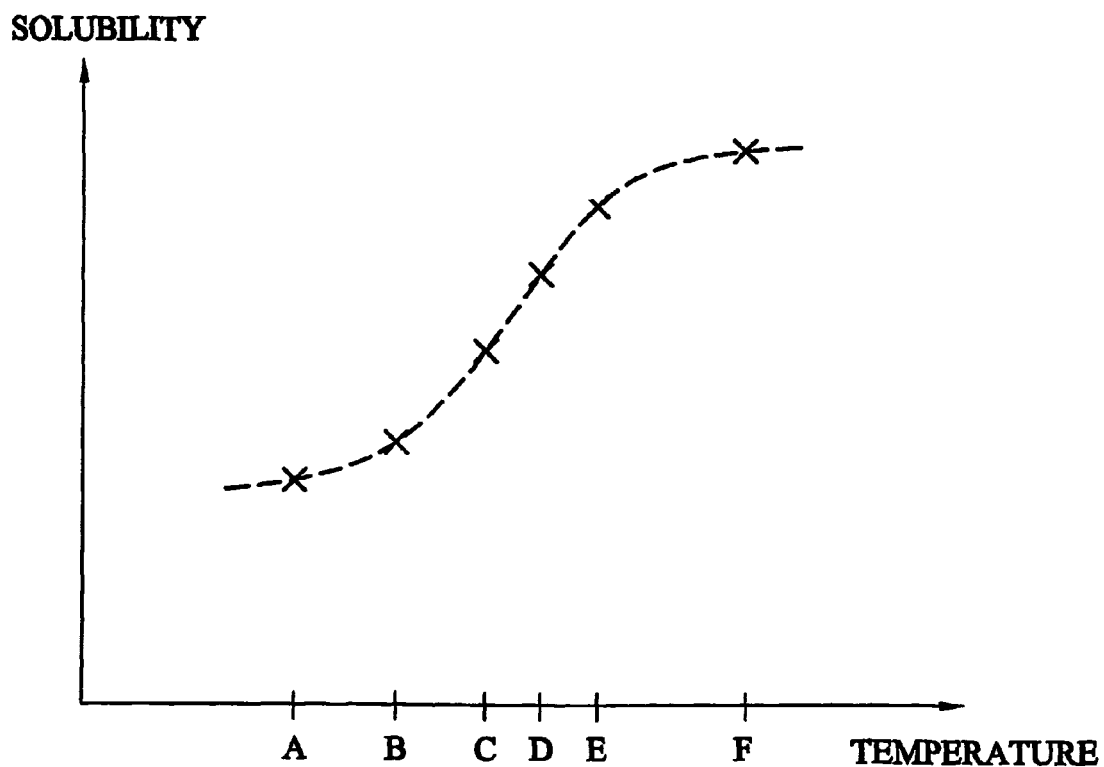
FIG. 11 is a typical solubility vs temperature profile obtained using the device.

The data obtained on analysis of the set of solubility measurements will be a set of points onto which a curve may be drawn as schematically illustrated in FIG. 11. It will be appreciated that, simply selecting an appropriate temperature and controlling temperature to this point, a solution of predetermined concentration of the solute may be prepared.

It will be appreciated from the above that use of the device described enables a solubility curve for solute/solvent combinations to be constructed rapidly with minimal man-power requirement. Furthermore, analyses may advantageously be undertaken on very small samples of solute.

The device may be used in experiments directed at preparing different polymorphs of materials as described below.

In a first embodiment, the solubility of a material in a solvent may be determined using device 2 as described above. Concentration of solute in a given solvent is known to be a key factor in determining conditions necessary for preparing different polymorphs. It is understood that at a known temperature, concentration of solute material dissolved in solvent is fixed and can be determined from the solubility curve constructed earlier. Thus, by selecting a known temperature for operation of the device 2, the concentration of solution preparable in receptacle 4 can be determined. Thus, with solvent and solute material in the device and the temperature fixed, the device is operated and the material/solvent combination equilibrated at the selected temperature.

Then, the valves controlling the supply of gas via ports 8, 10 are operated to cause the solution formed to pass through filter 5 so that a clear filtered solution at a fixed, known concentration is present in receptacle 4. Then, the solution may be subjected to a range of heating/cooling/equilibration cycles known to permit/cause the formation of different polymorphs and analyses undertaken as appropriate. Advantageously, by using robot control, hundreds of experiments may be undertaken using different conditions, with no user intervention.

In a second embodiment, the procedure of the first embodiment may be varied in order to carry out the analysis for polymorph determination in the outer receptacle 6. To this end, the material to be analysed is initially placed in the inner receptacle 4. The solvent is introduced as before and is mixed with the material as before. However, in this embodiment, after equilibration of the material/solvent at the temperature required to form a solution comprising a desired concentration of the material, the valves for controlling the supply of gas via ports 8, 10 are operated to cause the solution to pass into the outer receptacle 6. Then, the fixed concentration solution can be subjected to experimental conditions favourable to the preparation of polymorphs in the receptacle 6.

The receptacles 4 or 6 used in the first and second embodiments described may be adapted so that they can be removed from the device 2 and inserted directly into an apparatus, for example an XRD machine, used to analyse for different polymorphs, thereby avoiding any need to withdraw material from receptacles 4/6 for analysis.

Advantageously, a receptacle 4 may be used which is sized to be introduced directly into an XRD machine. For example it may comprise a fine glass capillary tube which includes a sintered material at its lower end arranged to define a filter.

In general terms receptacle 4 may be made out of any suitable material, such as metal, plastics, ceramic or glass. The filter may be made out of the same or a different material to that of the rest of the receptacle. For example it could be made out of paper or a sintered material. The filter may be made in any suitable size or shape and may be easily detachable from the rest of the receptacle for disposal. In one embodiment, the filter may be made out of injection moulded plastics and may be releasably securable to the rest of the receptacle.

The gas which is supplied via port 8, 10 is preferably an inert gas such as nitrogen or argon.

The device may have a maximum length of 15 cm, preferably 11 cm or less. The maximum width may be 5 cm, preferably 4 cm or less. The device may utilise 0.5 to 1.5 ml of solvent. However, bigger devices may be made if it is desired to analyse greater quantities of materials.

The device may be arranged to operate at up to 200° C.

The device and the methods described may be used in the pharmaceuticals industry to determine solubility and investigate polymorphs of an active drug substance. In this case, the solvent used may be any suitable pharmaceutically-acceptable solvent.

Although the device has been described in terms of assessing solubility and investigating polymorphs of a material in a single solvent, the device may be used with solvent mixtures. This may be particularly relevant to investigating polymorphs.

To increase the rate of analysis of a material a bank of devices 2, for example eight devices, may be assembled and each may be addressed by a single needle using a multi-needle robot system, suitably controlled by a single computer.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A device for analysing a material, comprising:
a first receptacle;
a second receptacle, said first and second receptacles being arranged for the passage of fluid therebetween, wherein said first receptacle is arranged within the second receptacle, and at least 40% of the volume of the first receptacle is contoured within the second receptacle;
a filtration means arranged to filter fluid passing between said first and second receptacles;
heating means for heating fluid in the device;
temperature assessment means for assessing the temperature of fluid in the device, wherein said first and second receptacles include respective first and second gas ports, wherein electronically-driven valves are provided for controlling the supply of gas via said first and second gas ports, and a gas travel path is defined from said first gas port via said first receptacle and said second receptacle to said second gas port, and wherein a first sealing means is arranged between the first and second gas ports to prevent the passage of gas in use directly from one port to the other.

2. A device according to claim 1, wherein said first receptacle is elongate and incorporates said filtration means.

3. A device according to claim 1, wherein said filtration means defines a part of an outer wall of the first receptacle and is positioned wholly within the confines of the cross-section of the first receptacle.

4. A device according to claim 1, wherein said filtration means is positioned within the second receptacle but does not abut the second receptacle to any extent.

5. A device according to claim 1, wherein an assembly comprising said first and second receptacles is releasably securable to a housing part which houses one or both of said heating means and said temperature assessment means.

6. A device according to claim 1, wherein said temperature assessment means is arranged to assess the temperature of fluid in the first and/or second receptacles and is positioned closer to the second receptacle than the first receptacle.

7. An assembly comprising a device according to claim 1, wherein said first and/or said second receptacles contain a material to be analysed and a fluid in which said material is at least partially soluble.

8. An assembly according to claim 7, which includes a control device for controlling operation of the heating means in dependence upon the temperature assessed by said temperature assessment means and said assembly includes a computer for storing data relating to temperature and time during operation of the device, wherein said computer also controls oscillation of liquid between the first and second receptacles.

9. An assembly according to claim 7, the assembly including a robot for delivering liquid to the device and/or for withdrawing liquid from the device.

10. An assembly according to claim 7, which includes a sample receptacle for receiving a sample removed from the device wherein said sample receptacle includes a dilution liquid.

11. An assembly comprising a plurality of devices according to claim 1 controlled by a computer.

12. A device according to claim 1, further comprising a computer configured to alternately open and close the electronically-driven valves to drive fluid back and forth across the filtration means.

13. A device according to claim 12, wherein the computer is configured to drive fluid across the filtration means at a frequency of at least 5 back and forth movements per minute.

14. A device according to claim 12, wherein the computer is configured to drive fluid across the filtration means at a frequency of at least 10 back and forth movements per minute.

15. A device according to claim 12, wherein the computer is configured to drive fluid across the filtration means at a frequency of at least 20 back and forth movements per minute.

16. A device according to claim 12, wherein the computer is configured to drive fluid across the filtration means at a frequency of at least 30 back and forth movements per minute.

17. A device according to claim 12, wherein the computer is configured to drive fluid across the filtration means at a frequency of at least 60 back and forth movements per minute.

18. A device according to claim 12, wherein the computer is configured to drive fluid across the filtration means at a frequency of 10 to 20 back and forth movements per minute.

19. A device according to claim 12, wherein the computer is configured to drive fluid across the filtration means at a frequency of 30 to 60 back and forth movements per minute.

* * * * *